United States Patent [19]

Shetty et al.

[11] Patent Number: 5,308,412
[45] Date of Patent: May 3, 1994

[54] METHOD OF SURFACE HARDENING COBALT-CHROMIUM BASED ALLOYS FOR ORTHOPEDIC IMPLANT DEVICES

[75] Inventors: H. Ravindranath Shetty; Walter H. Ottersberg, both of Warsaw, Ind.

[73] Assignee: Zimmer, Inc., Warsaw, Ind.

[21] Appl. No.: 30,912

[22] Filed: Mar. 15, 1993

[51] Int. Cl.⁵ .......................... B22F 1/00; A61F 2/00
[52] U.S. Cl. .................... 148/238; 420/436; 623/16; 623/18; 623/23
[58] Field of Search ............ 420/436; 148/238; 623/16, 18, 23

[56] References Cited

U.S. PATENT DOCUMENTS

| | | | |
|---|---|---|---|
| 3,713,175 | 1/1973 | Weisman | 420/436 |
| 4,668,290 | 5/1987 | Wang et al. | 75/235 |
| 4,714,468 | 12/1987 | Wang et al. | 420/439 |
| 4,743,308 | 5/1988 | Sioshansi et al. | 148/900 |
| 5,152,794 | 10/1992 | Davidson et al. | 623/22 |
| 5,152,795 | 10/1992 | Sioshansi et al. | 623/22 |
| 5,171,275 | 12/1992 | Ling et al. | 623/16 |
| 5,192,323 | 3/1993 | Shetty et al. | 623/16 |
| 5,198,308 | 3/1993 | Shetty et al. | 428/660 |

OTHER PUBLICATIONS

Wisbey et al. Biomaterials vol. 8 (1987) 477.
Guillermet et al. Z. Metallkoe 83 (Jan. 1992) 21.
C. D. Peterson, B. M. Hillberry, and D. A. Heck, "Component Wear of Total Knee Prostheses Using Ti–6A1–4V, Titanium Nitride Coated Ti–6A1–4V, and Cobalt–Chromium–Molybdenum Femoral Components," Journal of Biomedical Materials Research, vol. 22, 887–903 (1988).
Grill, A. Raven and R. Anvi, "Layer Structure and Mechanical Properties of Low Pressure" R. F. Plasma and Nitrided Ti–6A1–4V Alloy Surface and Coatings Technology 43/44 (1990) 745–755.

Primary Examiner—Upendra Roy
Attorney, Agent, or Firm—Todd A. Dawson

[57] ABSTRACT

A method of surface hardening cobalt-chromium based orthopedic implant devices, and a cobalt-chromium orthopedic implant device prepared by the disclosed method. An orthopedic implant device made of a cobalt-chromium or cobalt-chromium-molybdenum alloy, such as ASTM F-75 or ASTM F-799 is exposed to molecular nitrogen gas or ionized nitrogen at a process temperature and for a process time duration sufficient to enhance surface hardness and wear resistance properties, without the formation of a measurable nitrogen layer that tends to increase surface roughness and brittleness and diminish wear resistance properties. The process temperature is in the range of 500° F. to 2400° F., preferably about 1400° F., and the process time duration at the preferred process temperature is approximately 48 hours. The hardened surface of the cobalt-chromium-molybdenum implant occurs primarily due to nitride formation and solid solution hardening of the cobalt-chromium-molybdenum with nitrogen and oxygen, by dissolution.

21 Claims, 2 Drawing Sheets

METHOD OF SURFACE HARDENING COBALT-CHROMIUM BASED ALLOYS FOR ORTHOPEDIC IMPLANT DEVICES

BACKGROUND OF THE INVENTION

The present invention relates generally to cobalt-chromium (Co-Cr) based orthopedic implant devices and, more particularly, to a surface hardening process applicable to such devices, wherein surface hardness and wear resistance properties of the implant are enhanced with minimal loss in fatigue strength.

Cobalt-chromium based alloys have been used for orthopedic applications because of their strength, corrosion resistance, and biocompatability. However, under conditions of sliding wear or articulation of the cobalt-chromium alloy against other surfaces, particularly polymers, metals, ceramics, bone, and bone cement, the cobalt-chromium alloy will produce wear debris from articulating surfaces. Therefore, the surface of the alloys must be hardened in order to minimize wear.

In the past, surface hardening of cobalt-chromium based orthopedic implants has been achieved by depositing a titanium nitride coating on the surface of the implant, or by ion implantation of the cobalt-chromium substrate. Known surface hardening methods include gas nitriding, chemical salt bath nitriding, plasma or ion nitriding, and ion implantation. Of these methods, gas nitriding exhibits advantages over the other methods in terms of cost and ease of manufacture. For example, gas nitriding permits efficient batch processing of many parts concurrently in a furnace chamber; whereas, the ion implantation method requires line-of-sight bombardment of the workpiece, thereby limiting the dose uniformity and the number of parts that may be processed concurrently.

Gas nitriding of titanium based implants is well known. For example, surface hardening of titanium and its alloys has historically been performed by gas nitriding at elevated temperatures in the range of 700° C. to 1200° C. (1292° F. to 2192° F.). However, due to undesirable changes of certain physical and mechanical properties of the alloy based upon such high temperatures, a more recent process has been developed for surface hardening titanium alloys at a temperature of about 1100° F. for approximately eight hours. The hardened surface of the titanium implant occurs primarily due to solid solution hardening of the titanium with nitrogen by dissolution. This process is disclosed in detail in U.S. Pat. No. 5,912,323 issued on Mar. 9, 1993, and entitled "METHOD OF SURFACE HARDENING ORTHOPEDIC IMPLANT DEVICES", which disclosure is hereby incorporated by reference.

It is also known that cobalt-chromium based alloys, specifically ASTM F-75 and ASTM F-799 alloys, can be strengthened by adding nitrogen into the alloy in the molten state or diffusing nitrogen into the alloy in the solid state. Specifically, forming gas (15% hydrogen, 85% nitrogen) is utilized in combination with either ammonia or argon. However, such processes actually change the chemistry of the alloy by significantly increasing the weight percent of nitrogen present throughout the alloy. It has been found that when nitrogen is added in this manner, the fracture toughness of the alloy is reduced significantly because of the gross change in the chemistry of the alloy. It has also been found that hydrogen embrittlement and decarburization results from the hydrogen which is present in large amounts in dissociated (cracked) ammonia. If decarburization occurs, carbon is lost from the surface of the alloy, thereby decreasing the hardness of the alloy. Consequently, it is desirable to enhance the surface hardness of the cobalt-chromium material without substantial losses in fatigue strength or wear resistance properties.

SUMMARY OF THE INVENTION

Generally, the present invention provides a process for surface hardening an orthopedic implant device made of a cobalt-chromium alloy, wherein the surface hardness of the device is enhanced while maintaining corrosion resistance and fatigue strength. The invention also encompasses orthopedic implant devices in accordance with the claimed process.

Generally, the process of the present invention enhances the surface hardness of the cobalt-chromium implant device by thermal reaction of nitrogen gas within a specified temperature range. Consequently, surface hardness and wear properties are enhanced with minimal or no loss in fatigue strength More specifically, the use of a pure nitrogen gas at 1–2 psig. positive pressure in a specified temperature range prevents the formation of a substantial CrN layer on the surface that tends to increase surface roughness and brittleness and diminish wear resistance properties in orthopedic implant applications involving articulating joint surfaces. This method achieves enhanced surface hardness and wear properties without experiencing any gross, through-thickness (bulk) change in the nitrogen content of the implant.

An advantage of the surface hardening method of the present invention is that the surface of an orthopedic implant device made of a cobalt-chromium alloy is hardened without substantially affecting the mechanical, physical, and corrosion properties of the material.

Another advantage of the surface hardening method of the present invention is that the method is particularly adapted for use on load bearing prosthesis that contact with metals, ceramics, bone or polymers, due to a significant improvement in wear resistance coupled with minimal or no loss in fatigue strength.

A further advantage of the surface hardening method of the present invention is that it permits batch processing of orthopedic implant devices with uniform nitrogen dosage, as opposed to "line of sight" processing of parts in an ion implantation process.

Another advantage of the surface hardening method of the present invention is that the surface hardened cobalt-chromium alloy exhibits a lower contact angle and better wettability in water and serum solvents than nontreated alloys.

Yet another advantage of the surface hardening method of the present invention is that the surface hardened cobalt-chromium alloy exhibits a lower coefficient of friction against ultrahigh molecular weight polyethylene (UHMWPE) with serum lubrication than nontreated alloys.

Still another advantage of the surface hardening method of the present invention is that the method does not compromise the corrosion resistance of the alloy.

The invention, in one form thereof, provides an orthopedic implant device having enhanced surface hardness and wear resistance properties, wherein the implant comprises a cobalt-chromium substrate, an outer chromium nitride hardened surface layer substantially free of surface roughness, and a hardened diffusion layer underneath the outer surface layer. The hardened diffusion layer comprises a solid solution of nitrogen, oxygen, and carbon and is thicker than the outer layer. The implant is prepared by hardening the surface of the cobalt-chromium substrate by exposing the substrate to an atmosphere of substantially non-diluted molecular nitrogen gas or ionized nitrogen at a process temperature within the range of 500° F. to 2400° F. for a process time duration sufficient to achieve the hardened diffusion layer and the hardened outer surface layer. The process results in enhanced wear properties by substantially avoiding increased surface roughness.

The invention further provides, in one form thereof, a method of manufacturing a cobalt-chromium orthopedic implant device having enhanced wear resistance properties. The method includes an initial step of providing a cobalt-chromium substrate in the form of an orthopedic implant device, or component thereof. A surface hardening step is then performed. Specifically, the surface of the cobalt-chromium substrate is hardened by exposing the substrate to an atmosphere of substantially non-diluted molecular nitrogen gas or ionized nitrogen at a process temperature within the range of 500° F. to 2400° F. for a process time duration sufficient to achieve a hardened diffusion layer and a hardened outer surface layer. The surface of the cobalt-chromium substrate is then mechanically polished to get a highly polished smooth surface. The polishing is carried out in such a way that a minimum amount of metal is removed from the surface. In one aspect of the invention, the process temperature is approximately 1400° F., and the process time duration is approximately forty-eight hours.

DETAILED DESCRIPTION OF THE INVENTION

Figure 1:
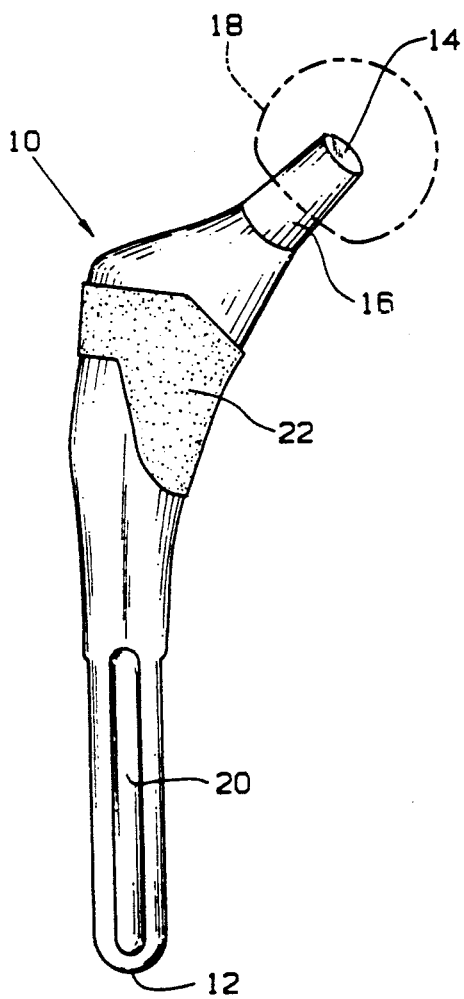
FIG. 1 is a side view of a femoral component for a hip prosthesis, representing a cobalt-chromium-molybdenum orthopedic implant device of the type to which the surface hardening process of the present invention is applicable.

Referring now to FIG. 1, there is shown an orthopedic implant device 10 fabricated from a cobalt-chromium alloy material and treated in accordance with the surface hardening method of the present invention. The term "cobalt-chromium material" as used herein is intended to encompass both cobalt-chromium based alloys and cobalt-chromium-molybdenum alloys, in particular. Two such cobalt-chromium-molybdenum alloys commonly used in orthopedic applications because of their strength, corrosion resistance, and biocompatability are ASTM F-75 and ASTM F-799. Commercial examples of ASTM F-75 alloys include The Hayes Stellite 21 the Haynes Stellite 6B (TM) alloy and the Ultimet (TM) alloy. In addition, an ASTM F-75 alloy is available having a high carbon and nitrogen content, and is known as Modified ASTM F-75 alloy.

In the disclosed embodiment of the present invention, orthopedic implant device 10 comprises a femoral component for a hip prosthesis of the type disclosed in U.S. Pat. No. 4,813,963, assigned to the same assignee as the present invention, the disclosure of which is hereby incorporated by reference. Generally, femoral component 10 includes a distal end 12, and a proximal end 14 having a neck 16 adapted to carry a ball 18 shown in phantom in FIG. 1. Femoral component 10 is intended to fit within an intramedullary canal of the femur (not shown) such that proximal end 14 extends outwardly from the intramedullary canal of the femur to cooperate with an acetabulum by means of ball 18. Femoral component 10 includes a plurality of longitudinally extending grooves 20 at distal end 12 and a porous surface 22 encircling the femoral component at an intermediate location along femoral component 10.

Figure 2:
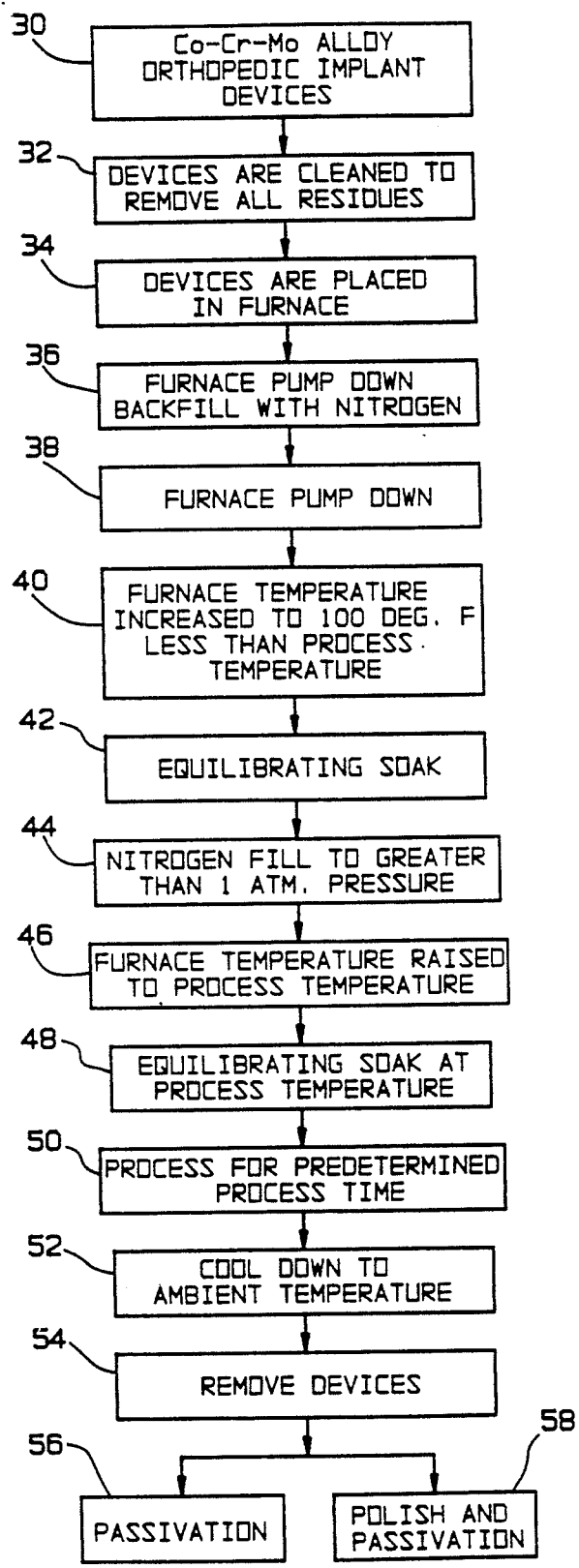
FIG. 2 is a diagrammatic representation of the process steps involved in an exemplary embodiment of the method of the present invention.

Referring now to FIG. 2, the steps for hardening the orthopedic implant device in accord with an exemplary embodiment of the present invention are diagrammatically illustrated. Generally, block 30 represents the first step of providing at least one cobalt-chromium orthopedic implant device or component part thereof. As previously discussed, ASTM F-75 or ASTM F-799 alloys are used for the implant device in the disclosed embodiment of the invention. Block 32 represents the next step of cleaning the device to remove all residues. Specifically, after an initial cleaning, the orthopedic implant devices are handled with gloved hands. The devices are then ultrasonically cleaned for 30 minutes in isopropyl alcohol and are then spray-dried to obtain a spot-free clean surface.

The next step of the process, represented by block 36 is placing the implant devices in a furnace. The furnace of the preferred embodiment is a vacuum furnace manufactured by Vacuum Furnace Systems (VFS) Corporation of Souderton, Pa. It is recommended that any furnace used for surface hardening the disclosed cobalt-chromium orthopedic implant devices be capable of maintaining a pressure level of $1 \times 10^{-6}$ Torr, a leak rate not exceeding 5 microns per hour, and a thermal uniformity of ±25° F. in vacuum and within ±50° F. in a nitrogen gas atmosphere, at operating temperatures.

As part of the step of placing the implant devices in the furnace, a furnace load is prepared, consisting of properly cleaned orthopedic implant devices assembled on suitable fixtures. The implant devices may or may not include any preattached bone ingrowth features, assembled on suitable fixtures. When placed in the furnace, the boundaries of the load must not extend beyond the uniform hot zone of the furnace. The number of parts in a load is dependent upon component size and fixture geometry. If desired, a predetermined mass of compacted titanium wire is equally divided and placed within and around the load to act as a getter. Cobalt-chromium alloy surface hardening can also be conducted without the getter material. Only materials which do not contaminate the cobalt-chromium alloy may be placed in the furnace with the load. Examples include outgassed high purity graphite, high purity alumina, zirconia, molybdenum, tantalum, and titanium.

After the load is placed in the furnace chamber, the next step is pumping down (evacuating) the chamber to $1 \times 10^{-5}$ Torr pressure and then backfilling with high purity nitrogen gas or ionized nitrogen to one atmosphere (or 0 psig), i.e., substantially non-diluted as represented by block 36. For purposes of this application, the term "non-diluted gas" shall include a non-rarefied gas. The step of block 36 is preferably performed at least twice, in order to remove any impurities. The chamber is then purged by once again pumping down or evacuating to $1 \times 10^{-5}$ Torr pressure, as represented by block 38. The minimum purity of molecular nitrogen gas used in the disclosed embodiment of the present invention is preferably 99.998 percent, with maximum allowable impurities of 10 ppm oxygen and 4 ppm water (vapor). In addition to these allowable impurities, the nitrogen gas may contain a trace of argon. The gas should also have a −90° F. dew point.

The next step, as represented by block 40 in FIG. 2, is heating the furnace at a rate of 25° F. per minute to a temperature of 1300° F.±50° F. and holding that temperature for 30 minutes to accomplish an equilibrating soak. The next step, represented by block 44, is filling the furnace with non-diluted nitrogen gas or ionized nitrogen to a pressure greater than one atmosphere pressure. A preferred range for the attained pressure is a minimum of 1 psig and a maximum of 2 psig; however, process pressure may be varied further without departing from spirit or scope of the invention. Block 46 of FIG. 2 represents the next step of heating the furnace at 20° F. per minute to a process temperature of 1400° F.±50° F. In the next step of the process, as described in block 48, an equilibrating soak is performed for 30 minutes at the process temperature.

According to the next step of the process, represented by block 50, the implant devices are processed for a predetermined process time duration at the process temperature. Specifically, a surface hardening cycle is run at the process temperature for various time periods depending upon the hardness and thickness of the hardened layer desired from the process. Preferably, the time period ranges from 8 to 48 hours. The hardening cycle is not considered to begin until any and all monitoring thermocouples are within the specified range for the process temperature.

Upon completion of the surface hardening cycle, the load may either be nitrogen quenched or furnace cooled, as the implant devices are cooled down, according to the step of block 52. The furnace is not opened until the temperature of the load is stabilized at 200° F.±25° F., or less, as measured by the highest reading monitoring thermocouple. The furnace may then be opened and the load removed, after which final passivation and processing is performed according to the steps of blocks 54 and 56, respectively. The final passivation step may also include polishing as shown in block 58.

While a specific combination of process temperature and time have been specified, it is appreciated that the cobalt-chromium alloy surface hardening method of the present invention can also be conducted at different temperatures in the range of 500° F. to 2400° F. at different nitrogen gas pressures, and for different time periods to produce the characteristic results of the present invention. This is graphically illustrated by the graph diagram of FIG. 3 showing the qualitative relationship between process temperature and time and the properties of cobalt-chromium orthopedic implant devices subjected to the surface hardening process of the present invention.

Figure 3:
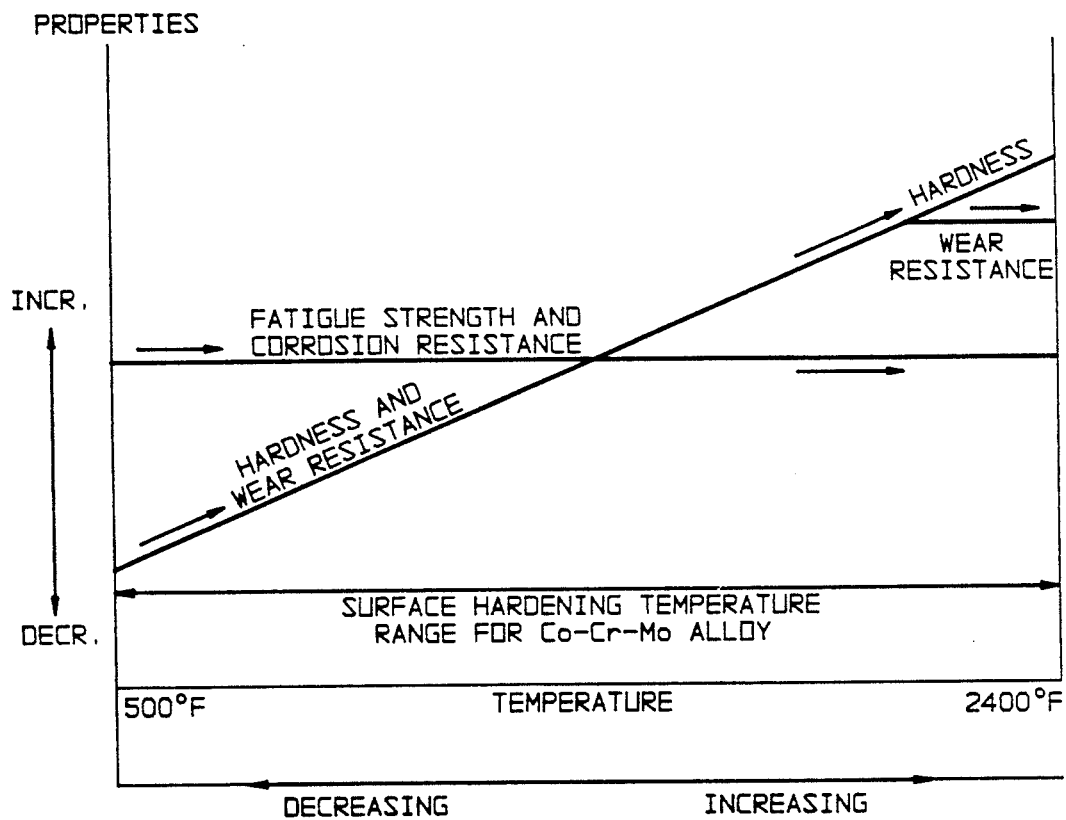
FIG. 3 is a graph diagram showing the qualitative relationship between process temperature and time, and properties of a cobalt-chromium orthopedic implant device subjected to the surface hardening process of the present invention.

Referring to FIG. 3, it can be seen that surface hardness and wear resistance of the cobalt-chromium alloy increases with increasing processing temperature within the range of 500° F. to 2400° F. in accordance with the surface hardening process of the present invention. However, beyond this temperature range, the formation of a measurable nitride layer on the surface increases surface roughness and brittleness as previously described, causing wear resistance to diminish. Fatigue strength and corrosion resistance generally remain constant within this temperature range. Similarly, the aforementioned changes in the properties are generally observed as process time is varied for a given process temperature within the specified temperature range.

In order to monitor the process, witness coupons of the same alloy and condition as the items in the load are placed in the furnace to assess the outcome of the process. One coupon is placed as closely as possible to the center of the load. The remaining coupons are placed in the hottest and coldest spots in the load as defined by previous survey. After the completion of the surface hardening cycle, the microhardness of the treated coupons is measured with a 2 gram load using a Knoop indentor. The surface hardening process of the present invention has been found to significantly increase the surface hardness of the cobalt-chromium material from its untreated condition. The hardness can be increased up to 5000 KHN depending upon the temperature, time, and nitrogen gas pressure used in the process. For instance, the average 2 gram Knoop surface hardness of the cobalt-chromium alloy processed at a process temperature of 1400° F. for a process time of 48 hours is approximately 1000 KHN, while the 2 gram Knoop surface hardness of the untreated alloy is in the range of 300–600 KHN.

Nitrogen depth profiles are also performed on the coupons to measure the depth concentration of nitrogen and oxygen, as by Electron Spectroscopy for Chemical Analysis (ESCA). The peak nitrogen concentration falls within the range of 5 atomic percent to 50 atomic percent and occurs at a depth between 100 and 1000 Angstroms from the alloy surface. An example of such a profile is exhibited in Tables I and II for a cobalt-chromium-molybdenum alloy, specifically ASTM F-75, for depths up to 2000 Angstroms (Table I) and 5000 Angstroms (Table II) below the surface of the alloy.

TABLE I

| Cycle | Depth in Angstroms (SiO$_2$ Equivalent) | Composition in Atomic Percent | | | | | |
|---|---|---|---|---|---|---|---|
| | | Mo | C | N | O | Cr | Co |
| 1 | — | — | 48.0 | 9.2 | 41.0 | 1.8 | — |
| 2 | 100 | 1.3 | 13.0 | 12.0 | 46.0 | 21.0 | 6.8 |
| 3 | 200 | 2.7 | 10.0 | 15.0 | 30.0 | 29.0 | 13.0 |
| 4 | 300 | 4.3 | 5.0 | 16.0 | 22.0 | 34.0 | 18.0 |
| 5 | 400 | 4.9 | 4.5 | 17.0 | 17.0 | 36.0 | 21.0 |
| 6 | 500 | 4.9 | 4.6 | 17.0 | 14.0 | 36.0 | 23.0 |
| 7 | 600 | 5.5 | 4.4 | 16.0 | 12.0 | 36.0 | 25.0 |
| 8 | 700 | 6.4 | 3.2 | 16.0 | 13.0 | 37.0 | 25.0 |
| 9 | 800 | 5.6 | 2.5 | 15.0 | 12.0 | 38.0 | 28.0 |
| 10 | 900 | 6.8 | .8 | 15.0 | 9.4 | 38.0 | 30.0 |
| 11 | 1000 | 6.9 | 3.2 | 14.0 | 8.6 | 36.0 | 31.0 |
| 12 | 1100 | 7.2 | 2.2 | 13.0 | 7.4 | 37.0 | 33.0 |
| 13 | 1200 | 7.8 | 3.3 | 14.0 | 6.6 | 35.0 | 34.0 |
| 14 | 1300 | 8.0 | 2.5 | 14.0 | 5.6 | 35.0 | 35.0 |
| 15 | 1400 | 8.3 | 1.4 | 13.0 | 5.2 | 34.0 | 38.0 |
| 16 | 1500 | 8.1 | 2.1 | 12.0 | 4.5 | 33.0 | 40.0 |
| 17 | 1600 | 7.6 | 1.3 | 13.0 | 5.0 | 34.0 | 39.0 |
| 18 | 1700 | 8.4 | 2.3 | 10.0 | 3.3 | 35.0 | 41.0 |
| 19 | 1800 | 8.8 | 2.0 | 11.0 | 2.4 | 35.0 | 41.0 |
| 20 | 1900 | 8.5 | 1.6 | 10.0 | 2.6 | 33.0 | 44.0 |
| 21 | 2000 | 7.9 | 2.0 | 11.0 | 2.4 | 33.0 | 43.0 |

TABLE II

| Cycle | Depth In Angstroms (SiO$_2$ Equivalent) | Composition in Atomic Percent | | | | | |
|---|---|---|---|---|---|---|---|
| | | Mo | C | N | O | Cr | Co |
| 1 | 0 | — | 49.0 | 8.7 | 40.0 | 2.2 | — |
| 2 | 1000 | 6.9 | 5.6 | 14.0 | 7.2 | 37.0 | 30.0 |
| 3 | 2000 | 9.7 | 1.8 | 9.8 | 2.2 | 32.0 | 45.0 |
| 4 | 3000 | 9.5 | 2.2 | 7.6 | — | 33.0 | 48.0 |
| 5 | 4000 | 9.5 | 1.8 | 8.4 | — | 34.0 | 46.0 |
| 6 | 5000 | 9.0 | 1.5 | 8.7 | — | 34.0 | 47.0 |

The fatigue strength of the cobalt-chromium alloy subjected to the process of the present invention was quantitatively tested by measuring the bending fatigue strength in units of kilopounds/in$^2$. It was determined that the disclosed low temperature surface hardening process results in minimal or no loss of fatigue properties.

The wear resistance of the cobalt-chromium alloy surface hardened in accordance with the disclosed process was tested by performing wear tests on a pin-on-disk wear tester, using ultrahigh molecular weight polyethylene (UHMWPE), bone, and bone cement pins to simulate actual implant conditions. Significant improvement in both sliding and abrasive wear resistance properties were observed.

Concerning the corrosion resistance properties of the cobalt-chromium subjected to the surface hardening process of the present invention, there does not appear to be any compromise of corrosion resistance. In fact, it has been found that surface hardened cobalt-chromium and cobalt-chromium-molybdenum alloys exhibit corrosion resistance as good as untreated cobalt-chromium alloys.

Contact angle measurements, which measure the angle between the surface of a liquid solvent (e.g. water, serum) and the surface of the alloy at the line of contact, were conducted in order to test the lubricity of the outer surface hardened layer of the alloys treated in the manner of the present invention. In the present case, water was the solvent of use. In general, the lower the contact angle, the more wettable the surface, which indicates greater lubricity. In an illustrative example, it has been found that a water droplet contact angle of about 44° is achieved for an alloy treated at 1400° F. for 48 hours. In contrast, the droplet contact angle for untreated alloys is generally about 70°.

In an effort to analyze the nature of the hardened surface produced by the aforementioned method of the present invention, treated samples of polished ASTM F-75 were analyzed through an Electron Spectroscopy for Chemical Analysis (ESCA) to identify phases or species present on the surface and to obtain surface chemistry versus depth plots of the samples including various spectra.

The surface hardening process of the disclosed preferred embodiment, as analyzed by the aforementioned method, produces a hardened surface layer, which is limited in thickness to a depth approximately 100 micrometers. The hardened surface layer is believed to include chromium nitride with different stoichiometries. It is also believed to have chromium oxide with different stoichiometries. The hardened surface layer is also believed to have some carbides in the form of chromium carbide.

Underneath the hardened surface layer is a hardened diffusion region that is hardened due to solid solution hardening of the cobalt-chromium alloy. The solid solution hardening elements in this case are nitrogen, oxygen, and carbon. This region extends several microns from the surface of the device. The ESCA analyses indicate that the hardened surface layer and harder diffusion region together constitute the desired hardened surface. Specifically, metallurgical changes on the surface of the treated cobalt-chromium implant device include the presence of chromium nitride, chromium oxide, chromium carbide, and solid solution of nitrogen in cobalt-chromium-molybdenum alloy, all of which together produce the desired hardening effect.

While the surface hardening process of the present invention is particularly applicable to orthopedic applications involving load bearing prostheses in articulating contact with bone, metals, ceramics or polymers, e.g., hip, knee, ankle, elbow, shoulder, wrist, finger, and toe joints, and may also be used to treat all cobalt-chromium and cobalt-chromium-molybdenum alloy fracture fixation devices as well.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

What is claimed is:

1. A method of manufacturing a cobalt-chromium orthopedic implant device having enhanced wear resistance properties, comprising the steps of:
   providing a cobalt-chromium substrate in the form of an orthopedic implant device; and
   hardening the surface of the cobalt-chromium substrate by exposing the cobalt-chromium substrate to an atmosphere of non-diluted molecular nitrogen gas at a process temperature within the range of 500° F. to 2400° F. for a process time duration sufficient to achieve a hardened outer surface layer and a hardened diffusion layer characterized primarily by solid solution hardening of the surface of the cobalt-chromium substrate by dissolution of nitrogen and oxygen in the cobalt-chromium substrate.

2. The method of claim 1 in which the orthopedic implant device is a load bearing member.

3. The method of claim 1 in which the orthopedic implant device makes articulating contact with one of a polymer, a ceramic or a metal.

4. The method of claim 1 in which said hardened surface region exhibits a peak nitrogen concentration within the range of about 5 atomic percent to about 50 atomic percent at a depth between 100 and 5000Å below the surface of the outer substrate.

5. The method of claim 1 in which said hardened surface region includes a hardened surface layer limited in thickness to a depth of approximately 100 micrometers and a hardened diffusion region underneath said hardened surface layer, said surface layer comprising chromium nitride, chromium oxide, and chromium carbide, and said hardened diffusion region comprising a solid solution of nitrogen, oxygen, and carbon in said cobalt-chromium substrate.

6. The method of claim 3 in which the polymer is ultrahigh molecular weight polyethylene (UHMWPE).

7. A method of manufacturing a cobalt-chromium orthopedic implant device having enhanced surface hardness and wear resistance properties, comprising the steps of:

providing a cobalt-chromium substrate in the form of an orthopedic implant device; and exposing the cobalt-chromium substrate to an atmosphere of molecular nitrogen gas at a process temperature and for a process time duration sufficient to cause nitrogen dissolution in the cobalt-chromium substrate without a substantial quantity of formation of a substantial quantity of chromium nitride on the surface of said the cobalt-chromium substrate, thereby enhancing the surface hardness and wear resistance properties of the cobalt-chromium substrate by substantially avoiding increased surface roughness and brittleness that would diminish the wear resistance properties.

8. The method of claim 7 in which said cobalt-chromium substrate comprises a cobalt-chromium-molybdenum alloy.

9. The method of claim 7 in which said cobalt-chromium alloy is one of ASTM F-75 and Modified ASTM F-75.

10. The method of claim 7 in which the process temperature is in the range of 500° F. to 2400° F.

11. The method of claim 7 in which the process time is approximately forty-eight hours.

12. The method of claim 7 in which the process temperature is approximately 1400° F. and the process time is approximately forty-eight hours.

13. The method of claim 7 in which said atmosphere of molecular nitrogen gas is provided at a process pressure within the range of 1 psig to 2 psig.

14. The method of claim 9 in which the cobalt-chromium alloy is ASTM F-799.

15. The method of claim 10 in which the process temperature is approximately 1400° F.

16. A method of increasing the surface hardness and wear resistance properties of an orthopedic implant device that is fabricated from a cobalt-chromium material, comprising the steps of:

providing a substrate of cobalt-chromium material in the form of an orthopedic implant device; and exposing the substrate to an atmosphere of non-diluted molecular nitrogen gas at a process temperature and for a process time duration sufficient to enhance both surface hardness and wear resistance properties of said substrate by nitrogen dissolution in the substrate by substantially avoiding increased surface roughness and brittleness and thereby diminishing wear resistance properties by the formation of a substantial quantity of chromium nitride on the surface of the substrate.

17. The method of claim 16 including the step of polishing the surface hardened implant device sufficiently to provide an ultrahigh finish to the device, thereby substantially improving the wear resistance of the implant.

18. The method of claim 16 in which the process temperature is in the range of 500° F. to 2400° F.

19. A method of manufacturing a cobalt-chromium orthopedic implant device having enhanced wear resistance properties, comprising the steps of:

providing a cobalt-chromium substrate in the form of an orthopedic implant device; and hardening the surface of the cobalt-chromium substrate by exposing the cobalt-chromium substrate to an atmosphere of ionized nitrogen at a process temperature within the range of 500° F. to 2400° F. for a process time duration sufficient to achieve a hardened outer surface layer and a hardened diffusion layer characterized primarily by solid solution hardening of the surface of the cobalt-chromium substrate by dissolution of nitrogen and oxygen in the cobalt-chromium substrate.

20. A method of manufacturing a cobalt-chromium orthopedic implant device having enhanced surface hardness and wear resistance properties, comprising the steps of:

providing a cobalt-chromium substrate in the form of an orthopedic implant device; and exposing the cobalt-chromium substrate to an atmosphere of ionized nitrogen at a process temperature and for a process time duration sufficient to cause nitrogen dissolution in the cobalt-chromium substrate without formation of a substantial quantity of chromium nitride on the surface of said the cobalt-chromium substrate, thereby enhancing the surface hardness and wear resistance properties of the cobalt-chromium substrate by substantially avoiding increased surface roughness and brittleness that would diminish the wear resistance properties.

21. A method of increasing the surface hardness and wear resistance properties of an orthopedic implant device that is fabricated from a cobalt-chromium material, comprising the steps of:

providing a substrate of cobalt-chromium material in the form of an orthopedic implant device; and exposing the substrate to an atmosphere of ionized nitrogen at a process temperature and for a process time duration sufficient to enhance both surface hardness and wear resistance properties of said substrate by nitrogen dissolution in the substrate by substantially avoiding increased surface roughness and brittleness and thereby diminishing wear resistance properties by the formation of a substantial quantity of chromium nitride on the surface of the substrate.

* * * * *